United States Patent [19]

Ohi

[11] Patent Number: 5,675,012

[45] Date of Patent: Oct. 7, 1997

[54] PROCESS FOR PRODUCTION OF CYANOPYRIDINE

[75] Inventor: Hideo Ohi, Shizuoka-ken, Japan

[73] Assignee: Ihara Chemical Industry Co., Ltd., Tokyo, Japan

[21] Appl. No.: 549,667

[22] PCT Filed: Mar. 29, 1995

[86] PCT No.: PCT/JP95/00587

§ 371 Date: Nov. 29, 1995

§ 102(e) Date: Nov. 29, 1995

[87] PCT Pub. No.: WO95/26340

PCT Pub. Date: Oct. 5, 1995

[30] Foreign Application Priority Data

Mar. 29, 1994 [JP] Japan .................... 6-082276

[51] Int. Cl.$^6$ .................................... C07D 213/84
[52] U.S. Cl. .................................... 546/286
[58] Field of Search .................................... 546/286

[56] References Cited

FOREIGN PATENT DOCUMENTS 60-28938  2/1985  Japan .................... 546/286

OTHER PUBLICATIONS

Organic Synthesis, vol. 4, p. 166. 1963.
Ann. Chem., vol. 487, pp. 127–133. 1931.

*Primary Examiner*—Zinna Northington Davis
*Attorney, Agent, or Firm*—Oblon, Spivak, McClelland, Maier & Neustadt, P.C.

[57] ABSTRACT

The present invention provides a process for producing a cyanopyridine represented by general formula (3)

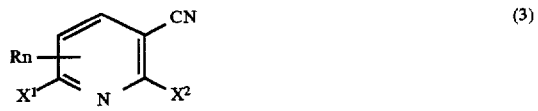

(wherein R is a hydrogen atom or a halogen atom; $X^1$ and $X^2$ are each a hydrogen atom or a halogen atom with a proviso that at least either of $X^1$ and $X^2$ is a halogen atom; n is an integer of 1 or 2), which process comprises reacting an ammonium halide with a trichloromethylpyridine represented by general formula (1)

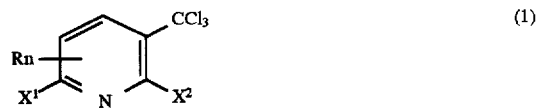

(wherein R, $X^1$, $X^2$ and n have the same definitions as given above) in the presence of a metal compound represented by general formula (2)

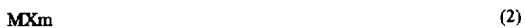

(wherein M is a copper atom or a zinc atom; X is a halogen atom or an oxygen atom; m is an integer of 2 or 1).

15 Claims, No Drawings

PROCESS FOR PRODUCTION OF CYANOPYRIDINE

This application is a 371 of PCT/JP95/00587 filed Mar. 29, 1995.

TECHNICAL FIELD

The present invention relates to a process for producing a cyanopyridine which is useful, for example, as an intermediate for production of agricultural chemicals or drugs.

BACKGROUND ART

For production of a cyanopyridine, there has been known, for example, a process which comprises reacting nicotinamide with phosphorus pentachloride to obtain 2-chloro-3-cyano-pyridine at a yield of 30% [Org. Syn., Coll., Vol. IV, p. 166 (1963)]. In this process, however, use of phosphorus pentachloride makes the operation troublesome; the conversion of acid amide group into nitrile group and the chlorination of ring proceed simultaneously, perchlorides are formed, and various side reactions take place; thus, the yield of intended product is not sufficient. Hence, the process has not been satisfactory for selective production of an intended cyanopyridine.

There is also known a process which comprises diazotizing a 3-amino-substituted pyridine derivative and subjecting the diazotization product to cyano substitution to produce a 3-cyanopyridine [An. Chem., Vol. 487, pp. 127–133 (1931)]. In this process, however, since the reaction proceeds momentarily to generate nitrogen gas explosively, the reaction is difficult to control; the yield of intended product is as low as several %; thus, the process has been insufficient as an industrial process.

The object of the present invention is to solve the problems of the prior art and provide a process for producing, in industry, a cyanopyridine safely and inexpensively with the side reactions being suppressed.

The present inventor made a study hardly in order to achieve the above object. As a result, the present inventor found out that the problems of the prior art can be solved by reacting a particular raw material, i.e. a trichloromethylpyridine having at least one halogen atom substituent at the 2- and 6-positions of the pyridine ring, with an ammonium halide in the presence of an oxide or halide of copper or zinc. A further-continued study has led to the completion of the present invention.

DISCLOSURE OF THE INVENTION

The present invention provides a process for producing a cyanopyridine represented by general formula (3)

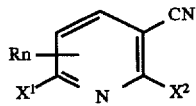
(3)

(wherein R is a hydrogen atom or a halogen atom; $X^1$ and $X^2$ are each a hydrogen atom or a halogen atom with a proviso that at least either of $X^1$ and $X^2$ is a halogen atom; n is an integer of 1 or 2), which process comprises reacting an ammonium halide with a trichloromethylpyridine represented by general formula (1)

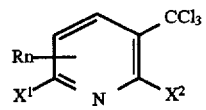
(1)

(wherein R, $X^1$, $X^2$ and n have the same definitions as given above) in the presence of a metal compound represented by general formula (2)

$$MX_m \quad (2)$$

(wherein M is a copper atom or a zinc atom; X is a halogen atom or an oxygen atom; m is an integer of 2 or 1).

BEST MODE FOR CARRYING OUT THE INVNETION

The present invention is hereinafter described in detail.

The trichloromethylpyridine represented by the above-mentioned general formula (1), used in the present invention is a trichloromethylpyridine of general formula (1) wherein the substituents $X^1$ and $X^2$ are each a hydrogen atom or a halogen atom including a chlorine atom, a fluorine atom, a bromine atom and an iodine atom (this halogen atom is hereinafter referred to simply as "halogen atom" in some cases) with a proviso that at least either of $X^1$ and $X^2$ is a halogen atom; the substituent R is a hydrogen atom or a halogen atom including a chlorine atom, a fluorine atom, a bromine atom and an iodine atom; n is an integer of 1 or 2 and therefore a plurality of Rs are possible [such a trichloromethylpyridine is hereinafter expressed simply as "trichloromethylpyridine (1)" in some cases]. Specific examples of the trichloromethylpyridine are 2-chloro-5-trichloromethylpyridine, 2-chloro-3-trichloromethylpyridine, 2-bromo-5-trichloromethylpyridine, 2-bromo-3-trichloromethylpyridine, 2-fluoro-3-trichloromethylpyridine, 2-fluoro-5-trichloromethylpyridine, 2,3-dichloro-5-trichloromethylpyridine, 2,6-dichloro-3-trichloromethylpyridine, 3-bromo-2-chloro-5-trichloromethylpyridine, 2,6-dibromo-3-trichloromethylpyridine, 2,3,6-trichloro-5-trichloromethylpyridine, 3-bromo-2,6-dichloro-5-trichloromethylpyridine, 2,3,4,6-tetrachloro-5-trichloromethylpyridine, 2,3,4,6-tetrafluoro-5-trichloromethylpyridine and 2,6-dichloro-3-fluoro-5-trichloromethylpyridine.

The ammonium halide used in the present process may be any of those compounds generally called as such. Specific examples thereof are ammonium chloride, ammonium bromide and ammonium iodide. Of these, ammonium chloride is easily available and preferred. The amount of ammonium halide used is, for example, 1–10 equivalents, preferably 1–3 equivalents, more preferably 1.2–1.5 equivalents per equivalent of the trichloromethylpyridine (1).

The metal compound represented by the above-mentioned general formula (2), used in the present process [said metal compound is hereinafter referred to simply as "metal compound (2)" in some cases] includes, for example, oxides or halides of copper or zinc, such as copper halide (e.g. cupric chloride, cuprous chloride, cupric bromide, cuprous bromide, cupric iodide or cuprous iodide), copper oxide (e.g. cupric oxide or cuprous oxide), zinc halide [e.g. zinc chloride, zinc bromide or zinc iodide], zinc oxide and the like. Of these, cupric chloride and cupric oxide are easily available and inexpensive, and are preferred. The amount of the metal compound (2) used is, for example, 0.05–10% by weight, preferably 0.1–5% by weight based on the trichloromethylpyridine (1).

In the present invention, the reaction is conducted at 100°–250° C., preferably at 170°–230° C. and at atmospheric pressure or under pressured condition, whereby the cyanopyridine represented by the above-mentioned general formula (3) [such a cyanopyridine is hereinafter referred to simply as "cyanopyridine (3)" in some cases] can be obtained easily.

In the operation of the present process, the order of the trichloromethylpyridine (1), the ammonium halide and the metal compound (2) added into the reactor has no restriction, and any of the materials may be added at first. Also in the reaction of the present process, use of solvent is optional. Since the reaction proceeds smoothly without using any solvent, use or no use of solvent can be decided in view of the scale of the reaction or the operation for isolation of the cyanopyridine (3) formed. Use of solvent is preferred in view of the yield of intended product. Incidentally, when a solvent is used, a solvent inert to the reaction, for example, sulfolane is suitable.

The cyanopyridine (3) produced in the present process includes, for example, 2-chloro-5-cyanopyridine, 2-chloro-3-cyanopyridine, 2-bromo-5-cyanopyridine, 2-bromo-3-cyanopyridine, 3-cyano-2-fluoropyridine, 5-cyano-2-fluoropyridine, 2,3-dichloro-5-cyanopyridine, 2,6-dichloro-3-cyanopyridine, 3-bromo-2-chloro-5-cyanopyridine, 2,6-dibromo-3-cyanopyridine, 2,3,6-trichloro-5-cyanopyridine, 3-bromo-2,6-dichloro-5-cyanopyridine, 2,3,4,6-tetrachloro-5-cyanopyridine, 5-cyano-2,3,4,6-tetrafluoropyridine and 2,6-dichloro-5-cyano-3-fluoropyridine.

Incidentally, some of the trichloromethylpyridines (1) used in the present process are commercially available. Those of no commercial availability can be obtained by halogenating 3-trichloromethylpyridine by a known method.

The cyanopyridine (3) obtained by the present process can be derived into an aminomethylpyridine by reducing the cyano group by a known method to convert said group into an aminomethyl group, and can further be easily derived therefrom into a compound which is an active ingredient for insecticides, for example, by the method described in Japanese Patent Application Kokai (Laid-Open) No. 154741/1992.

In the present process, since there is used, as a raw material, a particular pyridine derivative having at least one halogen atom substituent at the 2- and 6-positions of the pyridine ring, side reactions easily taking place in the reaction of a pyridine ring-containing compound, for example, decomposition and polymer formation taking place depending upon the temperature or operational conditions employed during the reaction are suppressed, whereby an intended reaction can be allowed to proceed smoothly. Incidentally, when there is used, as a raw material of the present process, a 3-trichloromethylpyridine whose 2- and 6-positions are both a hydrogen atom, no satisfactory result can be obtained as shown later in Reference Example.

The present invention is hereinafter described more specifically by way of Examples and Reference Example.

EXAMPLE 1

Production of 2-chloro-5-cyanopyridine

In a 200-ml reaction flask equipped with a thermometer, a Dimroth condenser and a stirrer were fed 46 g (0.2 mole) of 2-chloro-5-trichloromehtylpyridine, 16 g (0.3 mole) of ammonium chloride and 0.23 g (0.5% by weight) of cupric oxide. The mixture was reacted at 200° C. for 12 hours. The reaction mixture was cooled. At 130° C., 100 ml of xylene was added into the reaction flask. The mixture was cooled further. At 60° C., the mixture was filtered to remove a copper salt and excessive ammonium chloride. The filtrate (xylene layer) was concentrated. The resulting concentrate was subjected to distillation to obtain 20.3 g of 2-chloro-5-cyanopyridine as a fraction having a boiling point of 146°–150° C./15 mmHg. [Yield: 73.3%, colorless crystals having a melting point of 117°–118° C. (crystallization took place after distillation)]

EXAMPLES 2–6

Cyanopyridines (3) were produced in the same manner as in Example 1 except that the kind of trichloromethylpyridine (1) used (the amount used was kept at 0.2 mole), the kind and mole of ammonium halide used, and the kind and amount of metal compound (2) used were varied as shown in Table 1. The results are shown in Table 1.

TABLE 1

| Ex | Trichloromethyl-pyridine | Ammonium halide (mole) | Metal Comp. (wt. %) | Cyanopyridine | Yield (%) |
|---|---|---|---|---|---|
| 2 | 2,3-Dichloro-5-trichloromethylpyridine | Ammonium chloride (0.25) | Cupric chloride (1.5) | 2,3-Dichloro-5-cyanopyridine | 72.6 |
| 3 | 2,6-Dichloro-3-trichloromethylpyridine | Ammonium chloride (0.3) | Cupric chloride (0.3) | 2,6-Dichloro-3-cyanopyridine | 78.6 |
| 4 | 3-Bromo-2-chloro-5-trichloromethyl-pyridine | Ammonium chloride (0.3) | Cupric chloride (1.0) | 3-Bromo-2-chloro-5-cyanopyridine | 70.9 |
| 5 | 2,3,6-Trichloro-5-trichloromethyl-pyridine | Ammonium chloride (0.3) | Zinc oxide (0.4) | 2,3,6-Trichloro-5-cyanopyridine | 56.0 |
| 6 | 2,6-Dichloro-3-fluoro-5-trichloromethyl-pyridine | Ammonium bromide (0.3) | Zinc chloride (0.3) | 2,6-Dichloro-5-cyano-3-fluoro-pyridine | 50.1 |

EXAMPLE 7

Into a 200-ml reaction flask equipped with a thermometer and a stirrer were fed 46.1 g (0.2 mole) of 2-chloro-5-trichloromethylpyridine, 12.8 g (0.24 mole) of ammonium chloride, 0.46 g (1% by weight) of cupric oxide (CuO) and 10 ml of sulfolane. A reaction was allowed to take place at an oil-bath temperature of 180°–190° C. for 10 hours with stirring. After the completion of the reaction, the reaction mixture was cooled to 80° C., followed by addition of 200 ml of toluene and 100 ml of water to extract an intended product into the toluene layer. Then, the two layers were separated. The resulting toluene layer was washed sufficiently with water until no presence of sulfolane was confirmed by gas chromatography, then dried over anhydrous sodium sulfate, and subjected to distillation under reduced pressure to remove the extraction solvent. The resulting residue was further subjected to distillation under reduced pressure to obtain 21.1 g of an intended product as a fraction having a boiling point of 134° C./23 mmHg. (Yield: 76%)

REFERENCE EXAMPLE 1

A reaction was conducted for 12 hours in the same manner as in Example 1 except that 2-chloro-5- trichloromethylpyridine (0.2 mole) was replaced by 3-trichloromethylpyridine (0.2 mole). The resulting reaction mixture was analyzed by gas chromatography, which indicated that the amount of 3-cyanopyridine formed was 1% or less.

INDUSTRIAL APPLICABILITY

In the present invention, by a simple process of reacting a trichloromethylpyridine (1) with an ammonium halide in the presence of a metal compound (2), industrial production of a cyanopyridine with side reactions such as pyridine ring halogenation and the like being suppressed has been made possible. The present process, comprising no diazotization step, involves no danger such as explosion or the like and is an industrially safe process, and is useful as an industrial process for production of a cyanopyridine (3). Incidentally, the cyanopyridine (3) obtained by carrying out the present process, when reduced with hydrogen or the like, can be easily converted into an aminomethylpyridine which is an important intermediate for insecticides described, for example, in Japanese Patent Application Kokai (Laid-Open) No. 154741/1992.

I claim:

1. A process for producing a cyanopyridine represented by formula (3).

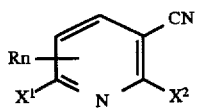
(3)

wherein R is a hydrogen atom or a halogen atom; $X^1$ and $X^2$ are each a hydrogen atom or a halogen atom with a proviso that at least either of $X^1$ and $X^2$ is a halogen atom; n is an integer of 1 or 2, which process comprises reacting an ammonium halide with a trichloromethylpyridine represented by formula (1)

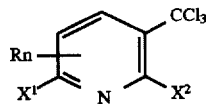
(1)

wherein R, $X^1$, $X^2$ and n have the same definitions as given above in the presence of a metal compound represented by formula (2)

$$MX_m \quad (2)$$

wherein M is a copper atom or a zinc atom; X is a halogen atom or an oxygen atom; m is an integer of 2 or 1.

2. The process of claim 1, wherein said reacting is conducted at 100°–250° C.

3. The process of claim 1, wherein said reacting is conducted at 170°–230° C.

4. The process of claim 1, wherein said reacting is conducted at atmospheric pressure.

5. The process of claim 1, wherein said reacting is conducted at a pressure above atmospheric pressure.

6. The process of claim 1, wherein 1–10 equivalents of said ammonium halide are reacted per equivalent of said trichloromethylpyridine.

7. The process of claim 1, wherein 1–3 equivalents of said ammonium halide is reacted per equivalent of trichloromethylpyridine.

8. The process of claim 1, wherein 1.2–1.5 equivalents of said ammonium halide is reacted per equivalent of said trichloromethylpyridine.

9. The process of claim 1, wherein the amount of said metal compound is 0.05–10% by weight based on said trichloromethylpyridine.

10. The process of claim 1, wherein the amount of said metal compound is 0.1–5% by weight based on said trichloromethylpyridine.

11. The process of claim 1, wherein n is 1.

12. The process of claim 1, wherein n is 2.

13. The process of claim 1, wherein said metal compound is cupric chloride.

14. The process of claim 1, wherein said metal compound is cupric oxide.

15. The process of claim 1, wherein said ammonium halide is ammonium chloride.

* * * * *